United States Patent
Orita

(10) Patent No.: US 9,440,840 B2
(45) Date of Patent: Sep. 13, 2016

(54) WATER DISPENSER
(71) Applicant: Kabushiki Kaisha Cosmo Life, Hyogo (JP)
(72) Inventor: Yoshinori Orita, Hyogo (JP)
(73) Assignee: Kabushiki Kaisha Cosmo Life, Hyogo (JP)
( * ) Notice: Subject to any disclaimer, the term of this patent is extended or adjusted under 35 U.S.C. 154(b) by 0 days.

(21) Appl. No.: 14/765,579
(22) PCT Filed: Dec. 2, 2013
(86) PCT No.: PCT/JP2013/082349
§ 371 (c)(1),
(2) Date: Aug. 4, 2015
(87) PCT Pub. No.: WO2014/136332
PCT Pub. Date: Sep. 12, 2014

(65) Prior Publication Data
US 2016/0002020 A1 Jan. 7, 2016

(30) Foreign Application Priority Data
Mar. 4, 2013 (JP) .................. 2013-041945

(51) Int. Cl.
*B67D 3/00* (2006.01)
*B67D 1/00* (2006.01)
(Continued)

(52) U.S. Cl.
CPC ............. *B67D 3/0038* (2013.01); *A61L 2/10* (2013.01); *B67D 1/0004* (2013.01);
(Continued)

(58) Field of Classification Search
CPC ... B67D 3/0032; B67D 3/0061; B67D 3/0038; B67D 3/0083; B67D 3/00; B67D 1/07; B67D 1/0004; B67D 1/0829; B67D 2210/00015; B67D 3/0058; A61L 2/10

USPC ......... 222/148, 146.1, 80–82, 83.5; 422/24; 141/18, 352, 364; 210/109, 257.1, 258
See application file for complete search history.

(56) References Cited

U.S. PATENT DOCUMENTS 5,232,125 A * 8/1993 Adams .............. B65D 41/0471
141/330
5,289,855 A * 3/1994 Baker ................. B67D 3/0032
141/18
(Continued)

FOREIGN PATENT DOCUMENTS

JP   2005-335713   12/2005
JP   2009-249033   10/2009
(Continued)

OTHER PUBLICATIONS

International Search Report issued Feb. 4, 2014 in International (PCT) Application No. PCT/JP2013/082349.
(Continued)

*Primary Examiner* — Kevin P Shaver
*Assistant Examiner* — Robert Nichols, II
(74) *Attorney, Agent, or Firm* — Wenderoth, Lind & Ponack, L.L.P.

(57) ABSTRACT

A water dispenser includes a raw water container having an inner tube a water outlet port of the raw water container. The inner tube is provided with a stepped portion having a smaller diameter at its portion closer to the interior of the raw water container, and a fastening belt portion formed contiguous to the stepped portion on the smaller diameter side thereof. The water server also includes a joint portion in the form of a cylindrical member including a straight portion (73) configured to be fitted tightly to the fastening belt portion, and provided with a water flow hole formed in a size so as not to cover the entire axial width of the fastening belt portion while the straight portion is being inserted into the fastening belt portion.

2 Claims, 10 Drawing Sheets

(51) Int. Cl.
    *B67D 1/08* (2006.01)
    *A61L 2/10* (2006.01)
(52) U.S. Cl.
    CPC ......... *B67D 1/0829* (2013.01); *B67D 3/0009* (2013.01); *B67D 3/0058* (2013.01); *B67D 1/0857* (2013.01); *B67D 1/0895* (2013.01); *B67D 2210/00015* (2013.01)

(56) References Cited

U.S. PATENT DOCUMENTS

| | | | |
|---|---|---|---|
| 5,370,270 | A | 12/1994 | Adams et al. |
| 5,868,281 | A * | 2/1999 | Bietzer ................. B65D 41/48 |
| | | | 141/352 |
| 5,937,921 | A * | 8/1999 | Guglielmini ......... B67D 3/0032 |
| | | | 141/351 |
| 6,167,921 | B1 | 1/2001 | Busick et al. |
| 6,602,425 | B2 * | 8/2003 | Gadgil ............... B01D 39/2068 |
| | | | 210/744 |
| 6,921,113 | B1 | 7/2005 | Vlasblom |
| 7,081,225 | B1 * | 7/2006 | Hollander ................. A61L 2/10 |
| | | | 210/748.11 |
| 2007/0267100 | A1 * | 11/2007 | Spear ................... B65D 47/141 |
| | | | 141/351 |
| 2009/0090690 | A1 * | 4/2009 | Walton ................. B67D 3/0032 |
| | | | 215/307 |

FOREIGN PATENT DOCUMENTS

| | | |
|---|---|---|
| JP | 2010-042859 | 2/2010 |
| JP | 2010-089842 | 4/2010 |
| JP | 2011-235905 | 11/2011 |
| JP | 4854820 | 1/2012 |

OTHER PUBLICATIONS

Extended European Search Report issued Jun. 29, 2016 in European Application No. 13876880.9.

* cited by examiner (a)

(b)

(c)

(a)

(b)

WATER DISPENSER

TECHNICAL FIELD

The present invention relates to a water dispenser which supplies drinking water from a replaceable raw water container filled with drinking water such as mineral water.

BACKGROUND ART

Conventionally, water dispensers have been used primarily in offices and in hospitals. With a growing interest in water safety and health in recent years, however, water dispensers are gaining popularity among ordinary households. A well-known type of water dispenser is one in which a replaceable raw water container is set in a housing, and drinking water filled in the raw water container is allowed to fall by gravity into a cold water tank housed inside the housing, or the drinking water is pumped up by a pump, as disclosed in the below-identified Patent Documents 1 and 2.

In the above mentioned water dispenser, a raw water supply passage which allows communication between the raw water container and the cold water tank includes a joint portion configured to be detachably connected to a water outlet port of the raw water container. The raw water container including a cap is generally used. As the cap, one including an inner tube protruding into the interior of the raw water container and defining a water outlet port of the raw water container, and a plug closing the water outlet port, is used. The plug includes a bottomed cylindrical portion configured to be fitted to the inner tube of the cap with its opening facing the exterior of the raw water container. The joint portion, which is configured to be inserted into this cap, comprises a cylindrical member including a straight portion configured to be fitted to the inner tube of the cap, a tip portion configured to be fitted inside the bottomed cylindrical portion of the plug so that the plug is stably engaged with the tip portion. The joint portion is connected to the water outlet port by being inserted into the inner tube of the cap. The tip portion of the joint portion inserted into the inner tube of the cap is pressed against the bottomed cylindrical portion of the plug, so that the tip portion is fitted inside the bottomed cylindrical portion, and the plug is stably engaged with the tip portion so as not to be disconnected from the joint portion. Once the plug is stably engaged with the tip portion, and then the plug is disconnected from the inner tube of the cap. Since the tip portion will be covered by the bottomed cylindrical portion when the tip portion is fitted therein, a water flow hole, through which raw water in the raw water container can be supplied into the joint portion, cannot be formed in the tip portion. Therefore, the water flow hole is formed in the straight portion of the joint portion and configured to open to the interior of the raw water container at a position away from the inner tube of the cap. As described above, when the joint portion is inserted into the raw water container to reach a position where the entire water flow hole opens to the interior of the raw water container, the straight portion of the joint portion is fitted to the inner tube of the cap with an interference fit. Due to the straight portion of the joint portion being brought into a close contact with the inner tube of the cap over the entire circumference thereof, a sealing effect to prevent the leaking of water from inside the raw water container can be obtained (for example, in water dispensers disclosed in below-identified Patent Documents 3 and 4).

Among these, a water dispenser is known in which, as shown in FIGS. 11(a) and (b), the inner peripheral surface of an inner tube 101 of a cap 100 is provided with a stepped portion 102 having a smaller diameter at its portion closer to the interior of the raw water container, and a fastening belt portion 103 formed contiguous to the stepped portion 102 on the smaller diameter side thereof. In this water dispenser, a fitting surface 105 is formed on the outer peripheral surface of the bottomed cylindrical portion of the plug 104, and configured to be fitted to the fastening belt portion 103 with an interference fit. The fitting between the fitting surface 105 and the fastening belt portion 103 provides a sealing effect to the raw water container before use. An engaging portion 106 is formed on the outer peripheral surface of the bottomed cylindrical portion and configured to engage with the stepped portion 102. During the transportation of a raw water container, the engagement between the engaging portion 106 and the stepped portion 102 prevents the plug 104 from being disconnected from the inner tube toward the interior of the raw water container. A guiding cylindrical portion 107 formed contiguous to the stepped portion 102 on the larger diameter side thereof guides the outer periphery of the a joint portion 108 such that the misalignment of the center of the joint portion 108 and the center of the inner tube 101 is controlled within a predetermined range. When the joint portion 108 is inserted into the raw water container such that an entire water flow hole 109 opens to the interior of the raw water container, as shown in FIG. 11(a), a sealing effect can be provided due to a straight portion 110 being brought into close contact with the fastening belt portion 103 over the entire circumference thereof. At this time, the straight portion 110 faces the guiding cylindrical portion 107. The straight portion 110 is not configured to be fitted to the guiding cylindrical portion 107 with an interference fit. If the straight portion 110 is configured to be fitted to the guiding cylindrical portion 107 with an interference fit, the guiding cylindrical portion 107 could be pushed inappropriately by the straight portion 110 in the radial direction of the inner tube, due to various errors, which in turn causes the fastening belt portion 103 to move away from the straight portion 110, possibly resulting in a loosening of the close contact between the fastening belt portion 103 and the straight portion 110 over the entire circumference thereof. As a result, the straight portion 110 may not be properly inserted into the inner tube 101 at the initial stage of the insertion process, and an insertion failure is more likely to occur.

PRIOR ART REFERENCES

Patent Documents

Patent Document 1: JP 2009-249033 A
Patent Document 2: JP 4854820 B
Patent Document 3: JP 2010-89842 A
Patent Document 4: JP 2010-42859 A

SUMMARY OF THE INVENTION

Problems to be Solved by the Invention

As shown in FIG. 11(b), in the above mentioned conventional water dispenser in which the fastening belt portion 103 is provided, the size of the water flow hole 109 (i.e., the axial distance d between the both ends of the water flow hole 109 of the joint portion) is generally set to about 10 mm, so that a sufficient amount of water is able to flow smoothly therethrough. On the other hand, it is preferred that the width L of the fastening belt portion 103 be as small as much as possible, within a range in which a desired sealing effect can be obtained. This is because, if the width L of the fastening belt portion 103 is too large, the straight portion 110 may not be smoothly inserted into the fastening belt portion 103, possibly resulting in a connection failure. Accordingly, the width L is generally set to less than 10 mm.

However, as a result of investigating various situations in which the water dispenser is used, the present inventors have found that there is a potential risk that proliferation of bacteria could occur between a gap formed between the guiding cylindrical portion 107 and the straight portion 110. In other words, when a new raw water container is connected to the joint portion 108, there is a moment at which the water flow hole 109 covers the entire axial width of the fastening belt portion 103 while the straight portion 110 is being inserted into the inner tube 101, due to the relationship between the values of the distance d and the width L being: d>L. At this moment, since the gap between the guiding cylindrical portion 107 and the straight portion 110 communicates with the interior of the raw water container, there are cases where raw water in the raw water container could get into the gap through the water flow hole 109, as shown by the arrow in the figure, to be kept in the gap due to the surface tension of the raw water. The raw water accumulated in the gap causes the proliferation of bacteria therein. When the raw water accumulated in the gap is evaporated and the bacteria therein are annihilated before the raw water container is replaced with a new one, there is no problem. However, in cases where the raw water in the raw water container is consumed rapidly and where the humidity is high, such as during the summer, the raw water accumulated in the gap may not be entirely evaporated until the next replacement. If the raw water container which has been used up is removed, with raw water accumulated in the gap, and with bacteria proliferating therein, the raw water in the gap is drawn by the straight portion 110 being pulled away, while the joint portion 108 is being disconnected from the inner tube 101, and spreads to the circumference of the water flow hole 109. When this happens, since the joint portion 108 is inserted into the inner tube 101 of a new raw water container immediately after removing the used up container, an undesired situation could occur in which drinking water in the new raw water container is contaminated with the bacteria which has spread around the water flow hole 109 in the straight portion 110.

Accordingly, an object of the present invention is to provide a water dispenser in which proliferation of bacteria is less likely to occur in the gap between the guiding cylindrical portion of the cap attached to the raw water container and the joint portion.

Means for Solving the Problems

In order to solve the above mentioned problems, the present invention has adapted the following constitution.

A water dispenser comprising: a replaceable raw water container; a cold water tank; and a raw water supply passage which allows communication between the raw water container and the cold water tank;

wherein a cap is attached to the raw water container, the cap comprising: an inner tube protruding into the interior of the raw water container and defining a water outlet port of the raw water container; and a plug closing the water outlet port;

wherein the raw water supply passage includes a joint portion configured to be detachably connected to the water outlet port;

wherein the inner peripheral surface of the inner tube is provided with a stepped portion having a smaller diameter at a portion thereof closer to the interior of the raw water container, and a fastening belt portion formed contiguous to the stepped portion on the smaller diameter side thereof;

wherein the plug comprises: a bottomed cylindrical portion configured to be fitted to the inner tube with the opening thereof facing the exterior of the raw water container; a fitting surface formed on the outer peripheral surface of the bottomed cylindrical portion so as to be fitted to the fastening belt portion with an interference fit; and an engaging portion formed on the outer peripheral surface of the bottomed cylindrical portion so as to engage with the stepped portion;

wherein the joint portion comprises a cylindrical member including a straight portion configured to be fitted to the fastening belt portion with an interference fit; and a tip portion configured to be fitted inside the bottomed cylindrical portion such that the plug is stably engaged with the tip portion;

wherein the straight portion is provided with a water flow hole configured to open to the interior of the raw water container at a position away from the inner tube; and wherein the water flow hole is formed in a size so as not to cover the entire axial width of the fastening belt portion while the straight portion is being inserted into the fastening belt portion.

With this arrangement, while the joint portion is being inserted into the inner tube of the cap attached to a new raw water container, the water flow hole does not cover the entire axial width of the fastening belt portion, and the gap between the guiding cylindrical portion and the straight portion does not communicate with the interior of the raw water container. Thus, when the joint portion is connected to the new raw water container, leaking of water into the gap between the guiding cylindrical portion and the straight portion can be avoided, thereby preventing the proliferation of bacteria in the gap.

When the joint portion is inserted into the inner tube, and the water flow hole passes through the fastening belt portion, raw water in the raw water container is brought into contact with the fastening belt portion. Further, there is a possibility that a heavy, new raw water container may not be accurately aligned with the joint portion when it is placed in the water dispenser, and the joint portion may be inserted into the raw water container with the straight portion thereof tilted inappropriately relative to the position of the fastening belt portion. If the joint portion is inserted into the raw water container with the straight portion thereof tilted inappropriately, it causes the fastening belt portion to deform, and thus, there is a potential risk that the fitting between the fastening belt portion and the straight portion could be loose at one portion therebetween in the circumferential direction, and raw water could leak from the loosened portion into the gap between the guiding cylindrical portion and the straight portion.

Therefore, in the above mentioned water dispenser, it is preferred that an ultraviolet light source be provided inside the joint portion; the straight portion be made of an ultraviolet light transmitting resin capable of transmitting ultraviolet light; and the inner peripheral surface of the inner tube be configured to be sterilized by ultraviolet light irradiated by the ultraviolet light source and transmitted through the straight portion. With this arrangement, the proliferation of bacteria in the fastening belt portion can be prevented. At the same time, even if unexpected leaking of water into the gap between the guiding cylindrical portion and the straight portion occurs, the proliferation of bacteria at the gap can also be prevented.

Effect of the Invention

In the water dispenser having the above mentioned constitutions, when the joint portion is connected to a new raw water container, leaking of water into the gap between the guiding cylindrical portion and the straight portion can be avoided, as described above. Accordingly, the present invention serves to provide a water dispenser in which proliferation of bacteria is less likely to occur in the gap.

BRIEF DESCRIPTION OF THE DRAWINGS

FIG. 5(a) is one showing the vicinity of a joint portion; FIG. 5(b) is one showing an alteration of an ultraviolet light reflecting portion; and FIG. 5(c) is one showing an alteration of an ultraviolet light source.

MODE FOR CARRYING OUT THE INVENTION

Figure 1:
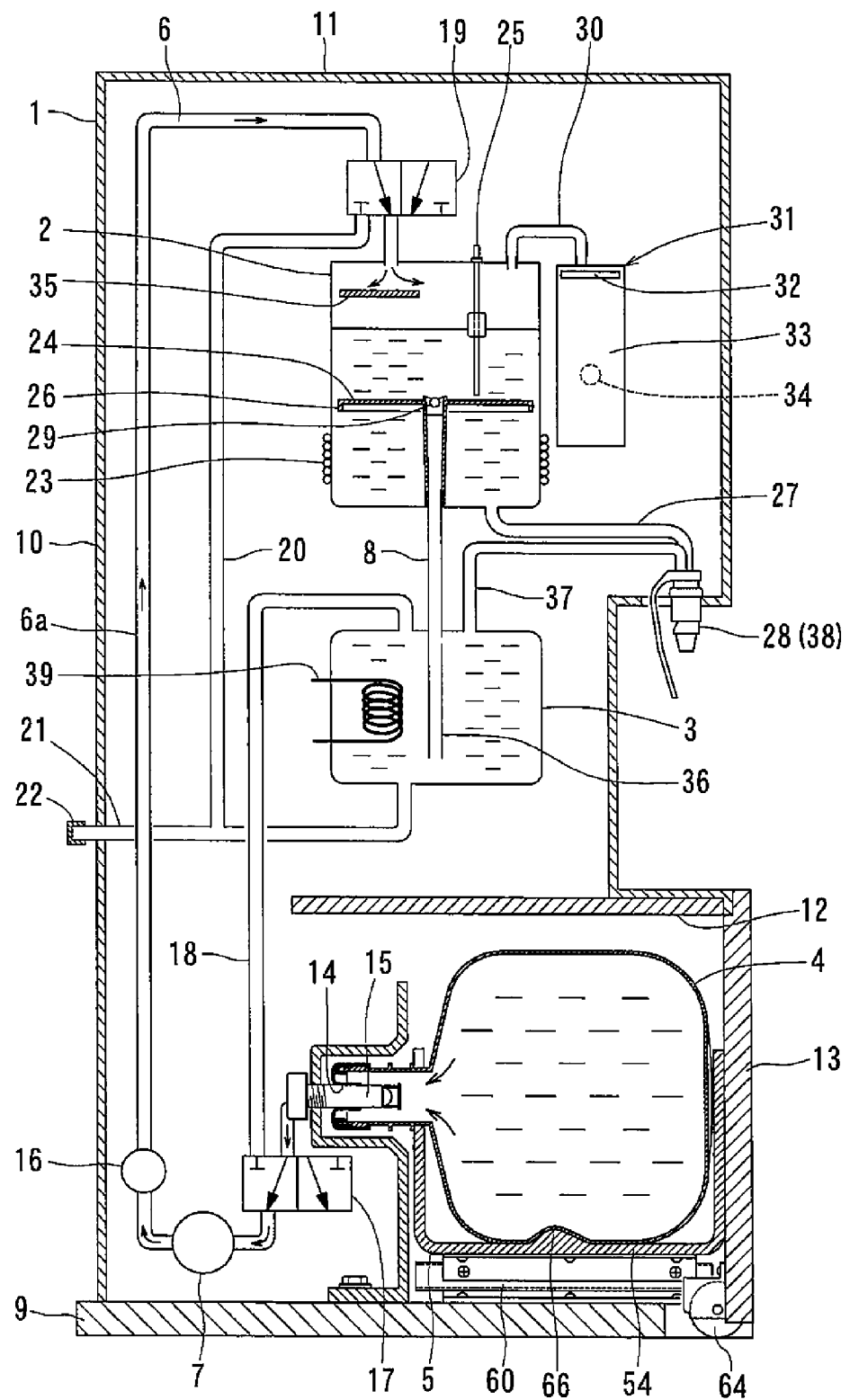
FIG. 1 is a sectional view of a water dispenser embodying the present invention, seen from the side.

A water dispenser embodying the present invention is shown in FIG. 1. The water dispenser includes: a vertically elongated housing 1; a cold water tank 2 and a hot water tank 3 both housed in the upper portion of the housing 1; a replaceable raw water container 4 housed in the lower portion of the housing 1; a container receiver 5 in which the raw water container 4 is placed; a raw water supply passage 6 which allows communication between the raw water container 4 and the cold water tank 2; a pump 7 provided in the raw water supply passage 6; and a tank connecting passage 8 connecting the cold water tank 2 to the hot water tank 3. The cold water tank 2 and the hot water tank 3 are arranged vertically such that the hot water tank 3 is positioned below the cold water tank 2.

The housing 1 includes a bottom plate 9, a peripheral wall 10 rising from the periphery of the bottom plate 9, and a top plate 11 provided at the top end of the peripheral wall 10. The peripheral wall 10 has, at the lower portion of its front side, a loading space 12 into and out of which the raw water container 4 can be moved, and a door 13 for opening and closing the loading space 12.

The raw water supply passage 6 includes a joint portion 15 configured to be detachably connected to a water outlet port 14 of the raw water container 4, and a pumping pipe 6a having one end thereof connected to the joint portion 15 and the other end thereof connected to the cold water tank 2. The pumping pipe 6a extends downward from the joint portion 15 and is then redirected upward so that it passes through a position lower than the joint portion 15. The pump 7 is provided in the pumping pipe 6a at its portion lower than the joint portion 15.

As the pumping pipe 6a, a silicone tube can be used. However, since silicone has an oxygen permeability, proliferation of bacteria is more likely to occur in the pumping pipe 6a due to the oxygen in the air that permeates through the silicone tube. Therefore, a metal pipe (such as a stainless steel pipe or a copper pipe) can be used as the pumping pipe 6a. With this arrangement, permeation of air through the wall of the pumping pipe 6a can be prevented, thereby allowing for an effective prevention of the proliferation of bacteria in the pumping pipe 6a. In addition, heat resistance of the pumping pipe 6a during the circulation of hot water can also be secured. Also by using a polyethylene tube or a heat-resistant, rigid polyvinyl chloride tube as the pumping pipe 6a, it is possible to prevent the permeation of air through the pipe wall of the pumping pipe 6a, thereby preventing the proliferation of bacteria in the pumping pipe 6a.

The pump 7 transfers the drinking water inside the pumping pipe 6a from the side of the raw water container 4 toward the cold water tank 2. A diaphragm pump can be used as the pump 7. While not shown, the diaphragm pump includes a driving device for reciprocating a diaphragm; a pump chamber whose volume is increased and decreased by the reciprocation of the diaphragm; a suction side check valve provided at the suction port of the pump chamber and configured to allow only the flow into the pump chamber; and a discharge side check valve provided at a discharge port of the pump chamber and configured to allow only the flow out of the pump chamber.

A flow rate sensor 16 is provided in the pumping pipe 6a on the discharge side of the pump 7. When there is no drinking water flowing in the pumping pipe 6a while the pump 7 is in operation, the flow rate sensor 16 is capable of detecting this fact.

A first switching valve 17 is provided in the raw water supply passage 6 at its portion between the joint portion 15 and the pump 7. Although the first switching valve 17 is placed at a position away from the joint portion 15 in the figures, the first switching valve 17 may be directly connected to the joint portion 15. A first bypass pipe 18 is connected to the first switching valve 17 and communicates with the hot water tank 3. The end portion of the first bypass pipe 18 on the side of the hot water tank 3 is connected to the upper surface of the hot water tank 3.

Figure 10:
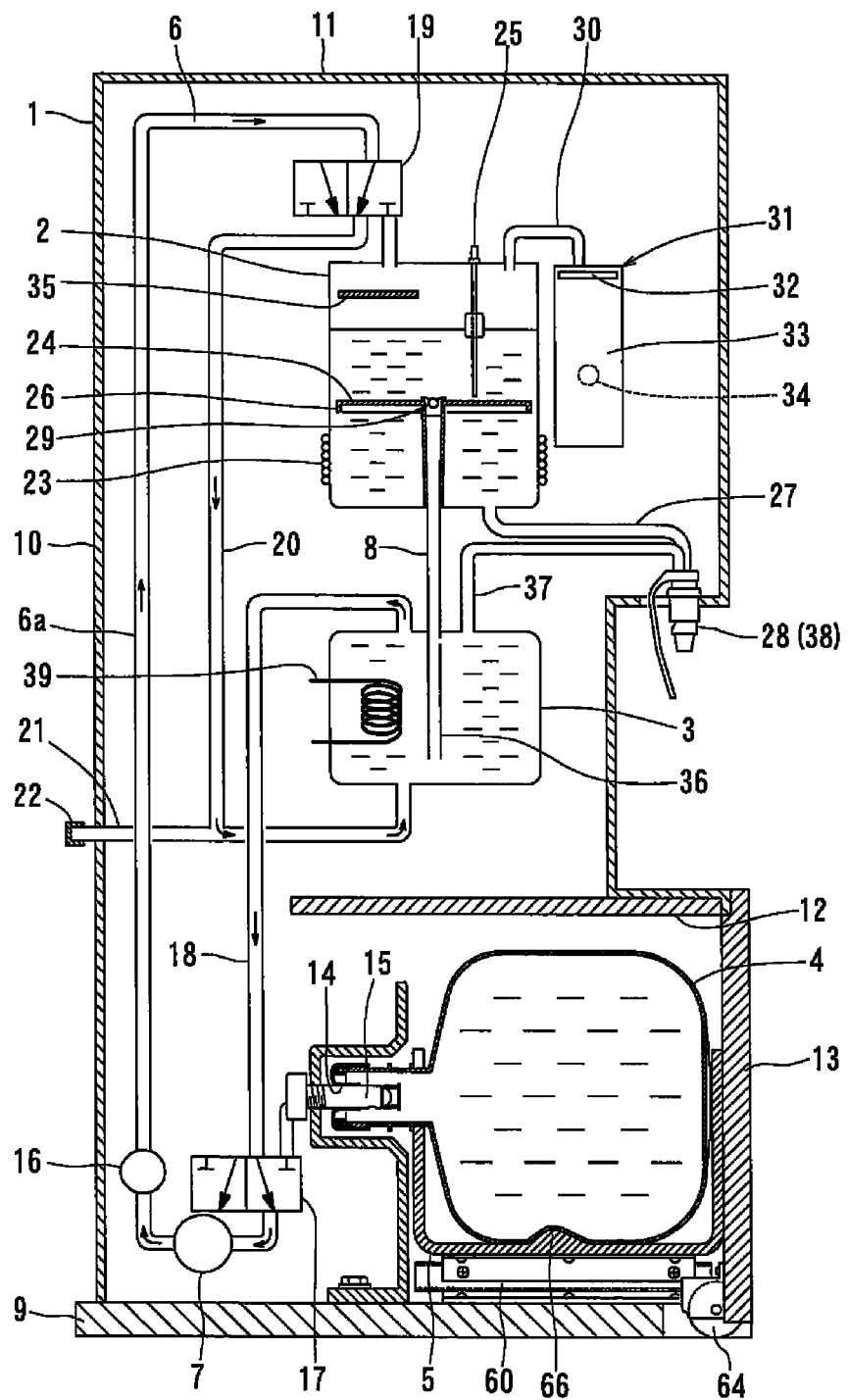
FIG. 10 is a sectional view of the water dispenser shown in FIG. 1, when it is in a sterilization operation mode.
Figure 11:
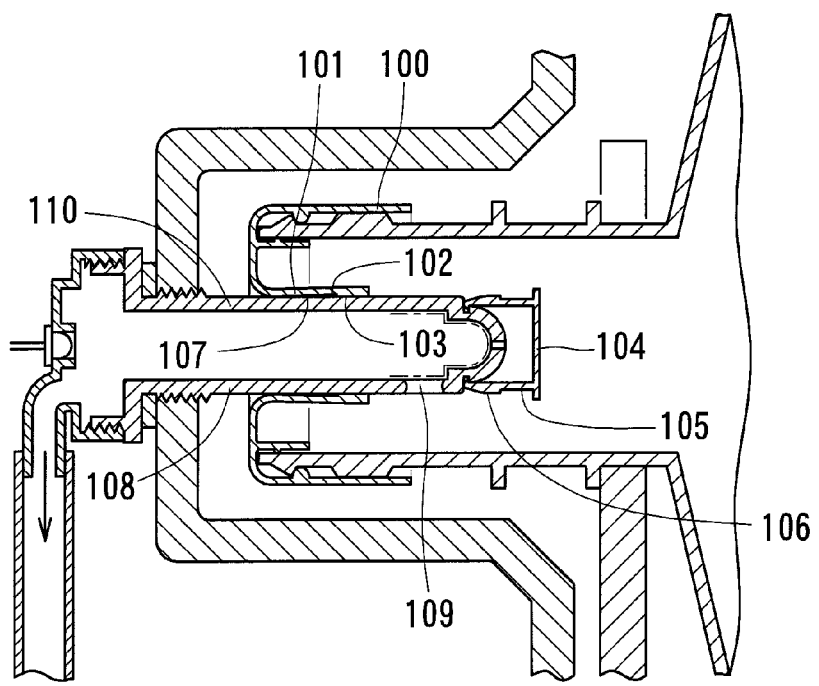
FIG. 11(a) is a sectional view of a conventional water dispenser, showing the state in which the connection of the joint portion to the raw water container has been completed.
FIG. 11(b) is a sectional view of the conventional water dispenser, showing the state during the connection of the joint portion to the raw water container.
Figure 11:
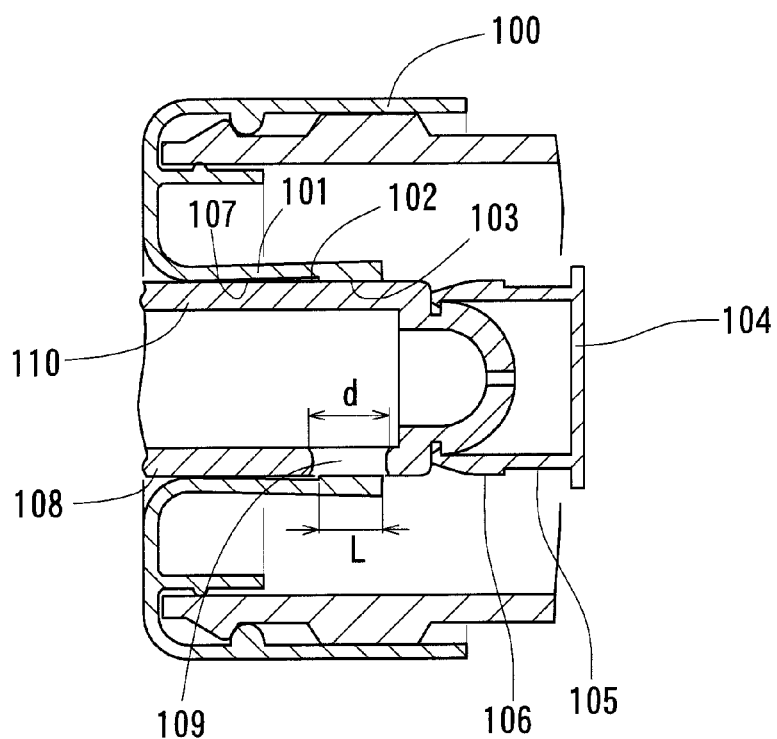

The first switching valve 17 is configured to be capable of switching the flow path between a normal operation mode (see FIG. 1) and a sterilization operation mode (see FIG. 10). In the normal operation mode, the first switching valve 17 allows communication between the joint portion 15 and the pump 7, while blocking communication between the first bypass pipe 18 and the pump 7; and in the sterilization operation mode, the first switching valve 17 blocks communication between the joint portion 15 and the pump 7, and allows communication between the first bypass pipe 18 and the pump 7.

A second switching valve 19 is provided at the other end portion of the raw water supply passage 6 positioned above the cold water tank 2, and it can be switched to carry out sterilization by hot water. A second bypass pipe 20 is connected to the second switching valve 19 and communicates with the hot water tank 3. The end portion of the second bypass pipe 20 on the side of the hot water tank 3 is connected to the bottom surface of the hot water tank 3. Further, a drain pipe 21 is connected to the second bypass pipe 20 and extends to the exterior of the housing 1. The outlet of the drain pipe 21 is closed with a plug 22. However, an on-off valve may be provided instead of the plug 22.

The second switching valve 19 is configured to be capable of switching the flow path between a normal operation mode (see FIG. 1) and a sterilization operation mode (see FIG. 10). In the normal operation mode, the second switching valve 19 allows communication between the pumping pipe 6a and the cold water tank 2, while blocking communication between the pumping pipe 6a and the second bypass pipe 20; and in the sterilization operation mode, the second switching valve 19 blocks communication between the pumping pipe 6a and the cold water tank 2, and allows communication between the pumping pipe 6a and the second bypass pipe 20.

Although each of the first switching valve 17 and the second switching valve 19 is illustrated as a single, three-way valve in the figures, a three-way valve assembly comprising a plurality of on-off valves may be used to achieve the same effect.

The cold water tank 2 contains air and drinking water in upper and lower layers. A cooling device 23 is attached to the cold water tank 2, and is configured to cool the drinking water contained in the cold water tank 2. Further, a baffle plate 24 is provided inside the cold water tank 2 and partitions the interior of the cold water tank 2 into upper and lower sections. The cooling device 23 is disposed at the lower outer periphery of the cold water tank 2, so that the drinking water inside the cold water tank 2 below the baffle plate 24 is maintained at a low temperature (about 5 degrees Celsius).

A water level sensor 25 is installed in the cold water tank 2 and configured to detect the water level of the drinking water accumulated in the cold water tank 2. When the water level detected by the water level sensor 25 falls to a predetermined level, the pump 7 is actuated, and drinking water is supplied from the raw water container 4 to the cold water tank 2. The baffle plate 24 prevents the low temperature drinking water cooled by the cooling device 23 and accumulated in the lower portion of the cold water tank 2 from being stirred by the normal temperature drinking water supplied from the raw water container 4 into the cold water tank 2, when the latter is supplied from the raw water container 4 to the cold water tank 2. The baffle plate 24 has a cylindrical suspended wall 26 extending downward from the outer peripheral edge of the baffle plate 24. By holding air in the space surrounded by the suspended wall 26, the insulation effect between the portions above and beneath the baffle plate 24 improves.

A cold water discharge passage 27 is connected to the bottom surface of the cold water tank 2 such that low temperature drinking water accumulated in the lower portion of the cold water tank 2 can be discharged to the outside through the cold water discharge passage 27. The cold water discharge passage 27 is provided with a cold water cock 28 capable of being operated from outside the housing 1, so that low temperature drinking water can be discharged from the cold water tank 2 into a cup or the like by opening the cold water cock 28. The capacity of the cold water tank 2 is lower than that of the raw water container 4, and is about from 2 to 4 liters.

A tank connecting passage 8 connecting the cold water tank 2 and the hot water tank 3 has a top end opening at the center of the baffle plate 24. A check valve 29 is provided at the end portion of the tank connecting passage 8 on the side of the cold water tank 2. The check valve 29 permits the flow of drinking water from the side of the cold water tank 2 toward the hot water tank 3, and restricts the flow of drinking water from the side of the hot water tank 3 toward the cold water tank 2. The check valve 29 prevents the loss of energy in the cold water tank 2 and the hot water tank 3, by preventing the high temperature drinking water in the hot water tank 3 from flowing into cold water tank 2 due to heat convection.

The hot water tank 3 is filled with drinking water. A heating device 39 is mounted to the hot water tank 3, and is configured to heat the drinking water in the hot water tank 3 so that the drinking water in the hot water tank 3 is maintained at a high temperature (about 90 degrees Celsius). While an example in which a sheathed heater is used as the heating device 39 is shown in the figures, a band heater may be used instead. The sheathed heater is a heating device including a heating wire housed in a metal pipe and configured to generate heat when energized, and is installed to extend through the wall of the hot water tank 3 and into the interior of the hot water tank 3. A band heater is a cylindrical heat generator in which a heating wire which generates heat when energized is embedded, and would be attached around the outer periphery of the hot water tank 3 in close contact therewith.

An air sterilization chamber 31 is connected to the cold water tank 2 through an air introduction passage 30. The air sterilization chamber 31 includes a hollow casing 33 in which an air inlet port 32 is formed, and an ozone generator 34 provided within the casing 33. The ozone generator 34 may be, for example, a low-pressure mercury lamp which irradiates ultraviolet light to the oxygen in the air to convert oxygen to ozone, or a silent discharge apparatus in which an AC voltage is applied between an opposed pair of electrodes covered with insulators to convert oxygen between the electrodes to ozone. The air sterilization chamber 31 is maintained in a state in which the casing 33 is filled with ozone at all times, by energizing the ozone generator 34 at regular intervals to generate ozone.

When the water level in the cold water tank 2 decreases, air is introduced into the cold water tank 2 through the air introduction passage 30 such that the pressure in the cold water tank 2 is maintained at atmospheric pressure. Since air introduced into the cold water tank 2 is sterilized with ozone by passing through the air sterilization chamber 31, the air inside the cold water tank 2 is maintained clean.

A diffuser plate 35 is provided in the cold water tank 2. The diffuser plate 35 is configured to diffuse the flow of drinking water transferred from the raw water supply passage 6 before it reaches the water surface of the drinking water accumulated in the cold water tank 2. The diffuser plate 35 increases the contact area between the drinking water and ozone contained in the air in the cold water tank 2 (i.e., ozone flowing into the cold water tank 2 through the air sterilization chamber 31), thereby improving the sanitation of the drinking water in the cold water tank 2.

The tank connecting passage 8 includes an in-tank pipe portion 36 extending downward from the upper surface of the hot water tank 3 through the interior of the hot water tank 3. The in-tank pipe portion 36 has an open lower end near the bottom surface of the hot water tank 3, thereby preventing the ascending flow of high temperature drinking water heated by the heating device 39 from directly flowing into the in-tank pipe portion 36 through the open lower end thereof.

A hot water discharge passage 37 is connected to the upper surface of the hot water tank 3 such that high temperature drinking water accumulated in the upper portion of the hot water tank 3 can be discharged to the outside through the hot water discharge passage 37. The hot water discharge passage 37 is provided with a hot water cock 38 capable of being operated from outside the housing 1, so that high temperature drinking water can be discharged from the hot water tank 3 into a cup or the like by opening the hot water cock 38. When drinking water is discharged from the hot water tank 3, the same amount of drinking water as the discharged drinking water flows into the hot water tank 3 from the cold water tank 2 through the tank connecting passage 8, so that the hot water tank 3 is maintained fully filled at all times. The capacity of the hot water tank 3 is about from 1 to 2 liters.

Figure 2:
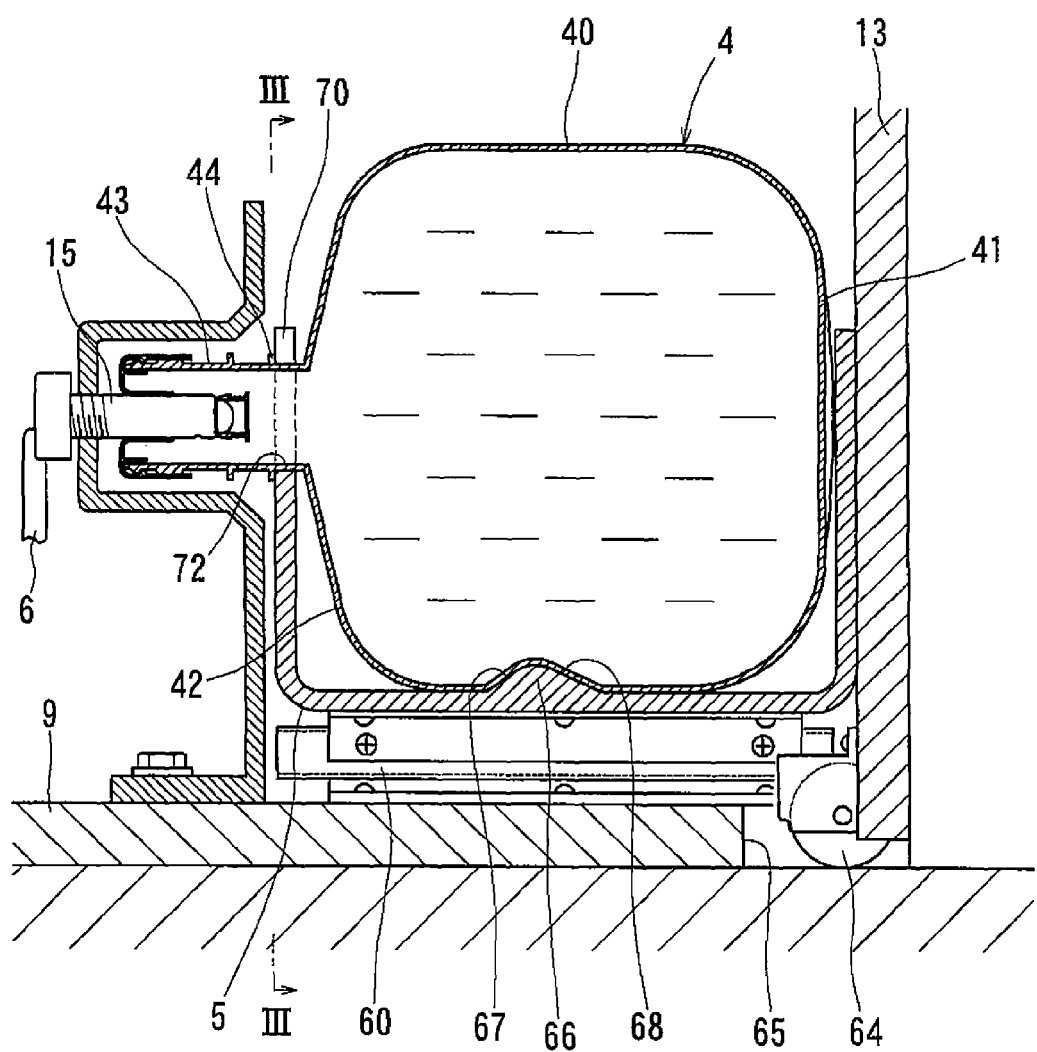
FIG. 2 is an enlarged sectional view of the water dispenser shown in FIG. 1, showing the vicinity of a container receiver.

As shown in FIG. 2, the raw water container 4 includes a hollow cylindrical trunk portion 40, a bottom portion 41 provided at one end of the trunk portion 40, and a neck portion 43 provided at the other end of the trunk portion 40 through a shoulder portion 42. A flange 44 is formed at the outer periphery of the neck portion 43. The trunk portion 40 of the raw water container 4 is formed flexible so that the raw water container 4 collapses as the amount of water remaining in the raw water container 4 decreases. The raw water container 4 as described above can be formed by blow molding of a polyethylene terephthalate (PET) resin or a polyethylene (PE) resin. The capacity of the raw water container 4 is from 10 to 20 liters when the container is fully filled.

Figure 5:
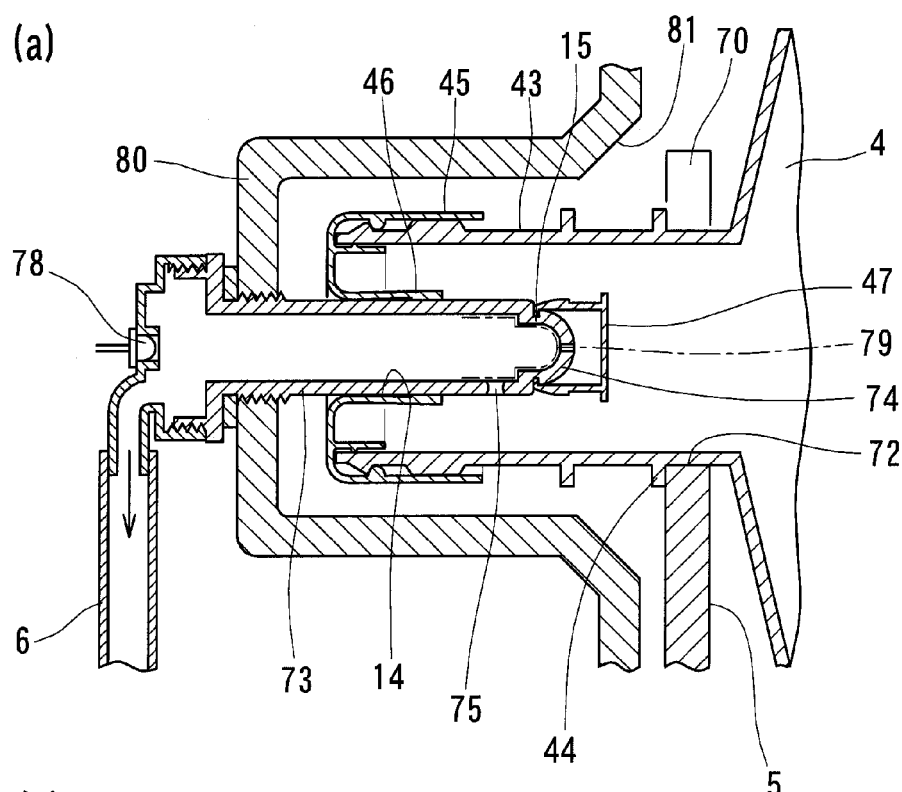
FIG. 5(a) to FIG. 5(C) are enlarged sectional views of the water dispenser shown in FIG. 2.
Figure 5:
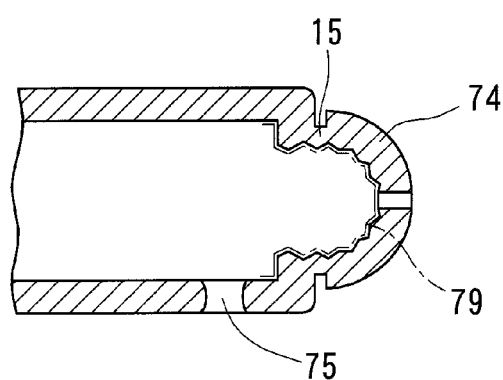
Figure 5:
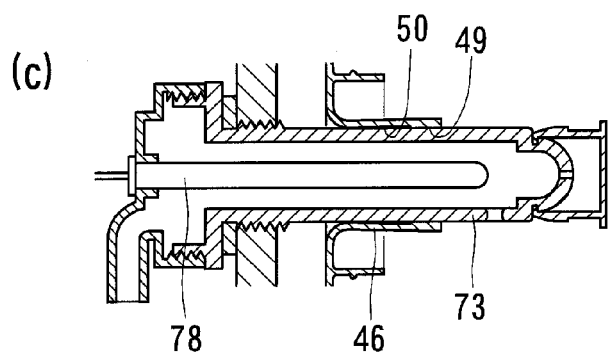

As shown in FIG. 5, a cap 45 is attached to the distal end of the neck portion 43 of the raw water container 4. An inner tube 46 is formed at the center of the cap 45. The inner tube 46 extends in parallel with the neck portion 43 toward the interior of the raw water container 4, and opens at its both ends. The inner tube 46 protrudes into the interior of the raw water container 4 and defines the water outlet port 14 of the raw water container 4. A plug 47 closing the water outlet port 14 is detachably fitted in the inner tube 46.

Figure 6:
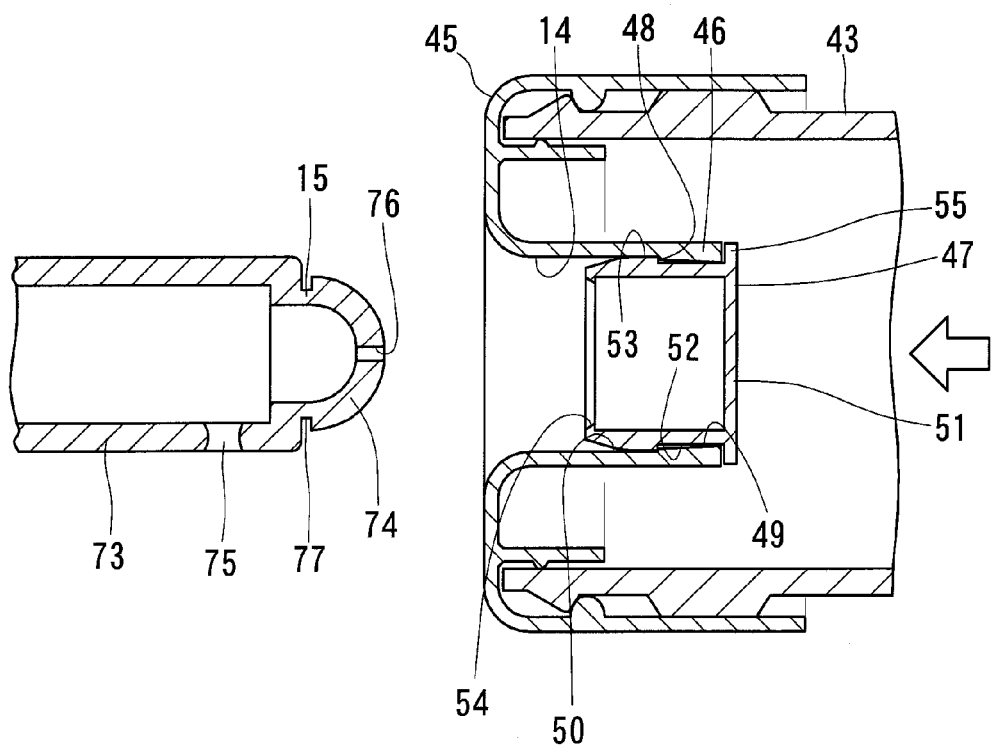
FIG. 6 is an enlarged sectional view of the water dispenser shown in FIG. 5, illustrating the process in which a raw water container is connected to the joint portion.

As shown in FIG. 6, the inner peripheral surface of the inner tube 46 is provided with a stepped portion 48 having a smaller diameter at its portion closer to the interior of the raw water container 4; a fastening belt portion 49 formed contiguous to the stepped portion 48 on the smaller diameter side thereof; and a guiding cylindrical portion 50 formed contiguous to the stepped portion 48 on the larger diameter side thereof. The plug 47 includes: a bottomed cylindrical portion 51 having a bottom and configured to be fitted to the inner tube 46 with its opening facing the exterior of the raw water container 4; a fitting surface 52 formed on the outer peripheral surface of the bottomed cylindrical portion 51 so as to be fitted to the fastening belt portion 49 with an interference fit; and an engaging portion 53 formed on the outer peripheral surface of the bottomed cylindrical portion 51 so as to engage with the stepped portion 48. The plug 47 further includes a claw portion 54 protruding inwardly from the inner peripheral surface of the bottomed cylindrical portion 51. An opposed piece 55 is formed on the outer peripheral surface of the plug 47 so as to axially face the end portion of the inner tube 46 when the bottomed cylindrical portion 51 is fitted to the inner tube 46. The fitting between the fitting surface 52 and the fastening belt portion 49 provides a sealing effect to the raw water container 4 before use. During the transportation of a new raw water container 4, the engagement between the engaging portion 53 and the stepped portion 48 prevents the plug 47 from being disconnected from the inner tube 46 toward the interior of the raw water container 4. In addition, by the opposed piece 55 getting caught on the end portion of the inner tube 46, the plug 47 is prevented from being disconnected from the inner tube 46 toward the exterior of the raw water container 4, during the transportation of the new raw water container 4.

Figure 3:
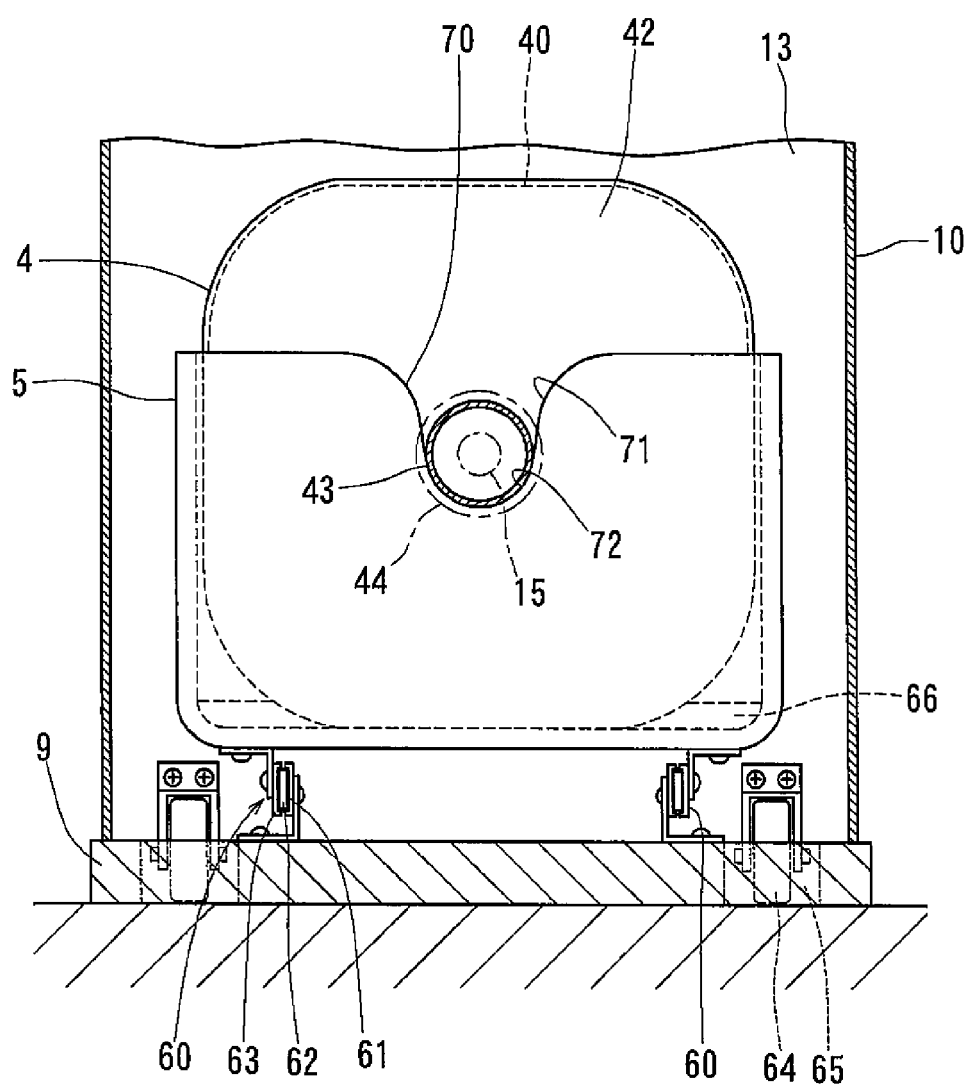
FIG. 3 is a sectional view of the water dispenser shown in FIG. 2, taken along the line III-III.

As shown in FIG. 2 and FIG. 3, the container receiver 5 includes: a bottom plate for supporting the raw water container 4 from below; side plates positioned on both sides of the raw water container 4; a front plate positioned forward of the raw water container 4; and a rear plate positioned rearward of the raw water container 4. As used herein, the words "forward" and "rearward" refer, respectively, to the directions toward and away from a user standing before the water dispenser. The container receiver 5 is supported by a right and left pair of slide rails 60 extending in the forward and rearward direction.

Figure 4:
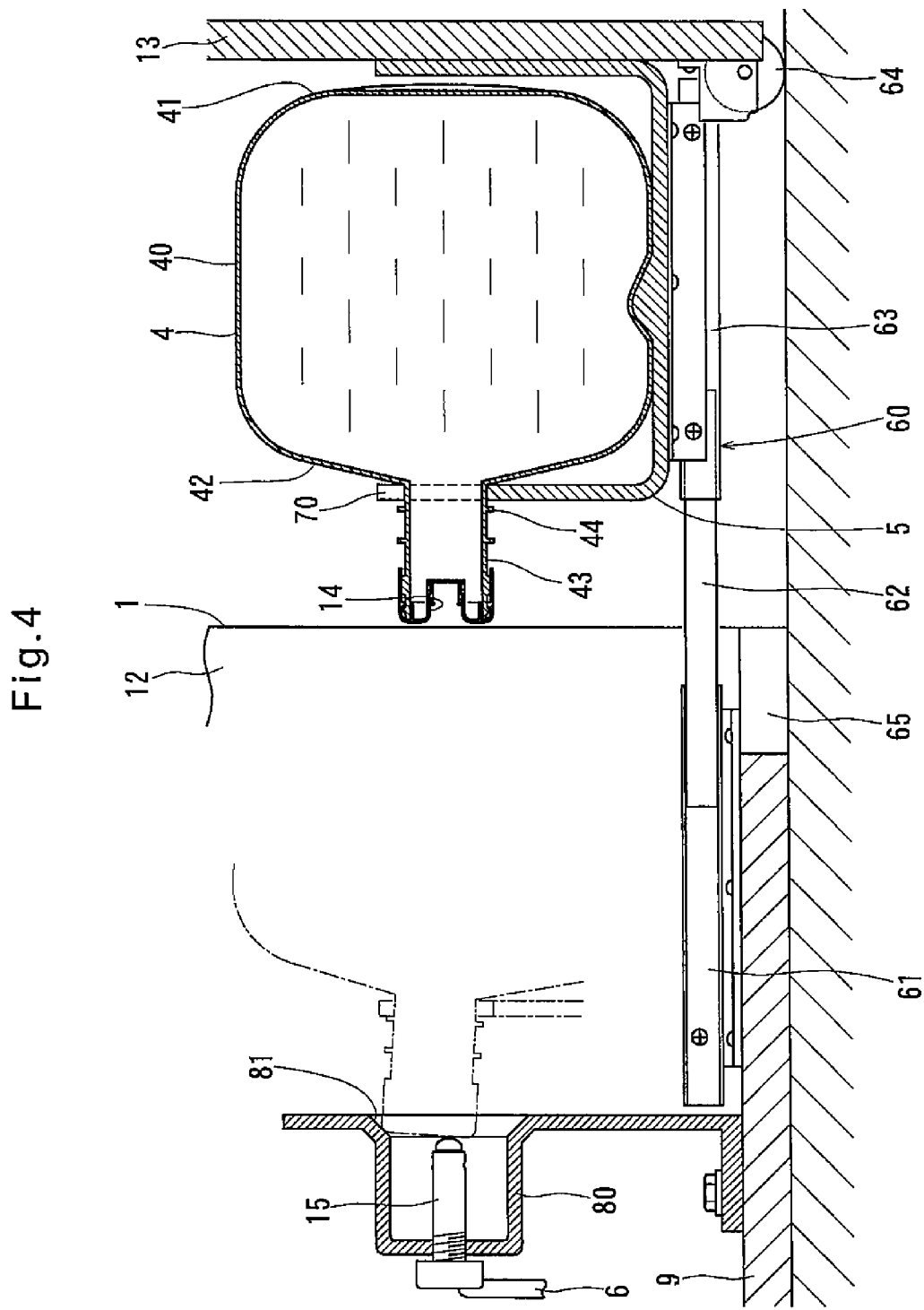
FIG. 4 is a sectional view of the water dispenser shown in FIG. 2, illustrating the state in which the container receiver has been pulled out of a housing.

As shown in FIG. 4, each of the slide rails 60 includes a fixed rail member 61 fixed to the bottom plate 9 of the housing 1 and extending in the forward and rearward direction, an intermediate rail member 62 slidably supported by the fixed rail member 61, and a movable rail member 63 slidably supported by the intermediate rail member 62. The movable rail members 63 are fixed to the bottom plate of the container receiver 5. The container receiver 5 is configured to be horizontally movable between a stowed position (the position shown in FIG. 2) in which the raw water container 4 is stowed inside the housing 1, and a pulled out position (the position shown in FIG. 4) in which the raw water container 4 is moved out of the housing 1, by the relative sliding movements of the three rail members 61, 62, and 63 constituting each of the slide rails 60.

The raw water container 4 is received in the container receiver 5, with the water outlet port 14 of the raw water container 4 facing the direction in which the container receiver 5 is moved from the pulled out position toward the stowed position (the rearward direction in the embodiment). At this time, the raw water container 4 is received in the container receiver 5 with the neck portion 43 directed horizontally.

The joint portion 15 is fixed in position inside the housing 1 such that it is disconnected from the water outlet port 14 of the raw water container 4 when the container receiver 5 has been moved to the pulled out position, as shown in FIG. 4, and it is connected to the water outlet port 14 of the raw water container 4 when the container receiver 5 has been moved to the stowed position, as shown in FIG. 2.

The door 13 of the housing 1 is fixed to the container receiver 5 so that the door 13 slides together with the container receiver 5. Thus, when the door 13 is pulled forward to open the loading space 12, the container receiver 5 is pulled out of the housing 1 at the same time. When the door 13 is pushed rearward to close the loading space 12, the container receiver 5 is stowed inside the housing 1 at the same time.

Wheels 64 are attached to the lower portion of the door 13 so as to be kept in rolling contact with the surface on which the housing 1 is placed. When the container receiver 5 is pulled out of the housing 1 and a load (such as the weight of a fully filled raw water container 4 and/or the weight of a person) acts on the container receiver 5, the wheels 64 prevent the housing 1 from falling by supporting the load. Recesses 65 for stowing the wheels 64 are formed in the bottom plate 9 of the housing 1.

As shown in FIG. 2, a protrusion 66 is provided on the bottom plate of the container receiver 5 to extend across the middle of the trunk portion 40 of the raw water container 4. The upper surface of the protrusion 66 is formed with a slope 67 sloping downward from the apex of the protrusion 66 toward the joint portion 15, and a slope 68 sloping downward from the apex of the protrusion 66 in the direction away from the joint portion 15. The slope 68, namely the slope on the side opposite from the joint portion 15, is less steep than the slope 67 on the side of the joint portion 15, and has an inclination angle of 30° or less.

As shown in FIG. 3, the rear plate of the container receiver 5 is provided with a notch 70 opening to the upper edge of the rear plate. The notch 70 includes an introduction portion 71 narrowing gradually downwardly from the upper edge of the rear plate, and a semicircular restricting portion 72 formed contiguous to the lower side of the introduction portion 71, and configured to be fitted to the outer periphery of the neck portion 43 of the raw water container 4. The restricting portion 72 is fitted to the portion of the neck portion 43 closer to the trunk portion 40 than is the flange 44.

The restricting portion 72 is formed into a circular arc shape having a diameter smaller than the outer diameter of the flange 44. The restricting portion 72 is fitted to the outer periphery of the neck portion 43 to fix the position of the neck portion 43 in the radial direction, thereby preventing the position of the water outlet port 14 of the raw water container 4 from being displaced from the position of the joint portion 15, when the raw water container 4 is connected to the joint portion 15. Further, as shown in FIG. 2, the restricting portion 72 engages with the flange 44 to fix the position of the neck portion 43 in the axial direction, thereby restricting the movement of the water outlet port 14 of the raw water container 4 in the direction in which the water outlet port 14 is disconnected from the joint portion 15.

As shown in FIG. 5, the joint portion 15 comprises a cylindrical member including a straight portion 73 having a cylindrical outer wall surface; and a tip portion 74 having a smaller outer diameter than that of the straight portion 73. The axial direction of the joint portion 15 is a horizontal direction. The outer diameter of the straight portion 73 is larger than the inner diameter of the fastening belt portion 49. Therefore, the straight portion 73 is configured to be fitted to the fastening belt portion 49 with an interference fit. The straight portion 73 and the guiding cylindrical portion 50 are not configured to be fitted to each other with an interference fit. The straight portion 73 is provided with a water flow hole 75 configured to open to the interior of the raw water container 4 at a position away from the inner tube 46. The water flow hole 75 is entirely provided only in the lower half portion of the joint portion 15, and not in the upper half portion thereof. When the entire water flow hole 75 opens to the interior of the raw water container 4, the straight portion 73 is fitted to the fastening belt portion 49 such that the straight portion 73 is brought into close contact with the entire circumferential surface of the fastening belt portion 49, and therefore, a sealing effect can be obtained. At this time, the straight portion 73 faces the guiding cylindrical portion 50. Since the fastening belt portion 49 is formed on the inner tube 46 protruding into the interior of raw water container 4, when the straight portion 73 is inserted into the inner tube 46 to push the fastening belt portion 49 in the radial direction, the inner tube 46 is bent toward the interior of the raw water container, in the diameter-increasing direction. As a result, the contact pressure between the straight portion 73 and the fastening belt portion 49 is increased, particularly in the vicinity of the stepped portion 48, thereby providing an excellent sealing effect. This arrangement allows for reducing the interference between the straight portion 73 and the fastening belt portion 49, and facilitates the insertion of the straight portion 73 into the inner tube 46.

Figure 7:
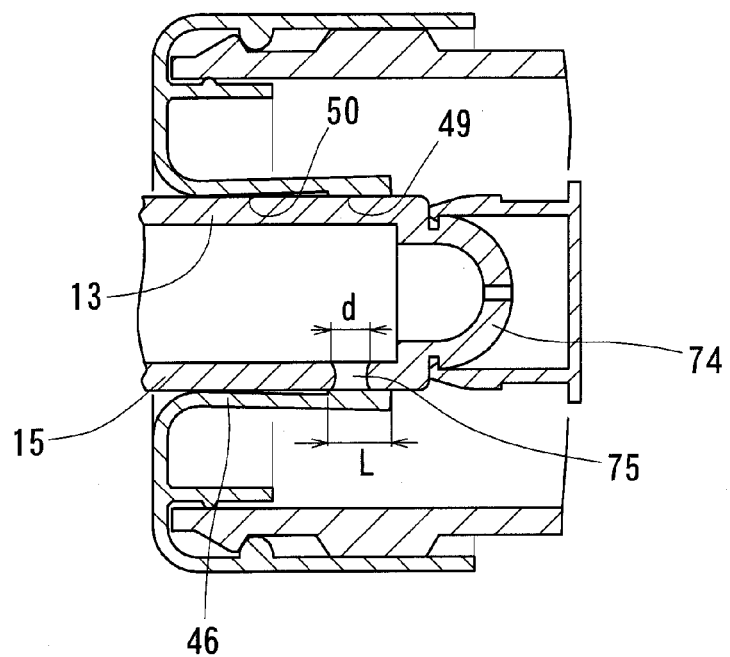
FIG. 7 is an enlarged sectional view of the water dispenser shown in FIG. 6, illustrating the state in which the joint portion is brought into contact with a plug attached to a water outlet port of the raw water container.

As shown in FIG. 6 and FIG. 7, the tip portion 74 has a hemispherical head. A through hole 76 is formed through the center of the head of the tip portion 74 to communicate with the interior and the exterior of the joint portion 15. The diameter of the through hole 76 is set to 1.0 mm or less. Further, a constricted neck portion 77 in the shape of a circumferential groove is formed at the boundary between the tip portion 74 and the straight portion 73, and configured to engage with the claw portion 54 of the plug 47. The guiding cylindrical portion 50 guides the outer periphery of the joint portion 15 such that misalignment between the center of the joint portion 15 and the center of the inner tube 46 is controlled within a predetermined range. The guidance by the guiding cylindrical portion 50 facilitates the head of the tip portion 74 to be stably fitted inside of the bottomed cylindrical portion 51, and the straight portion 73 to be stably fitted to the fastening belt portion 49. When the head of the tip portion 74 of the joint portion 15 is inserted into the interior of the bottomed cylindrical portion 51, pushing through the claw portion 54, the constricted neck portion 77 engages with the claw portion 54. When the constricted neck portion 77 is engaged with the claw portion 54, the plug 47 is stably and inseparably fitted to the joint portion 15 by the tip portion 74. Once this state is established, the plug 47 is then disconnected from the inner tube 46.

As shown in FIG. 7, the water flow hole 75 is preferably formed in a size so as not to cover the entire axial width of the fastening belt portion 49 while the straight portion 73 is being inserted into the fastening belt portion 49. In other words, the axial distance d between the end of the water flow hole 75 closest to the tip portion 74 and the end of the water flow hole 75 closest to the root of the joint portion 15 is preferably shorter than the axial width L of the fastening belt portion 49. With this arrangement, while the joint portion 15 is being inserted into the inner tube 46 of a new raw water container 4, the water flow hole 75 will never cover the entire axial width of the fastening belt portion 49, thus preventing the gap between the guiding cylindrical portion 50 and the straight portion 73 from communicating with the interior of the raw water container 4. This in turn prevents the leaking of water into the gap between the guiding cylindrical portion 50 and the straight portion 73, when the joint portion 15 is connected to the new raw water container 4, and therefore, proliferation of bacteria is less likely to occur in the above mentioned gap.

If the water flow hole 75 is formed in the shape of a circle, for example, the inner diameter of the water flow hole 75 corresponds to the distance d. Therefore, the distance d should be determined so as to satisfy the relation: $d<L$. The difference between the values L and d, i.e., $L-d$, is not limited: provided a sealing effect can be obtained between the fastening belt portion 49 and any portion of the straight portion 73 over the entire circumference thereof, at all times while the straight portion 73 is being inserted into the fastening belt portion 49; and raw water can be smoothly supplied into the joint portion 15. In cases where raw water is pumped up by the pump 7, for example, raw water can be pumped up into the joint portion 15 even if the sectional area of the passage through the water flow hole 75 is small. Therefore, in such cases, even if the distance d is set to 5 mm or less, it causes no problem in supplying raw water. In general, the value of the width L is set to be within the range of more than 5 mm and less than 10 mm. Thus, if the distance d is set to 5 mm or less, it is possible to obtain a sealing effect effective to prevent the leaking of water into the gap between the guiding cylindrical portion 50 and the straight portion 73.

As shown in FIG. 5(a), an ultraviolet light source 78 is provided inside the joint portion 15, on the bottom surface at the root of the joint portion 15. The straight portion 73 is made of an ultraviolet light transmitting resin. The inner peripheral surface of the inner tube 46 is configured to be sterilized by the ultraviolet light irradiated by the ultraviolet light source 78 and transmitted through the straight portion 73. This prevents the proliferation of bacteria at the fastening belt portion 49. Further, even if unexpected leaking of water into the gap between the guiding cylindrical portion 50 and the straight portion 73 occurs, the proliferation of bacteria in this gap can also be prevented. The interior of the joint portion 15 is also sterilized by the ultraviolet light of the ultraviolet light source 78.

The ultraviolet light source 78 may be an ultraviolet light emitting diode or a mercury lamp. As the ultraviolet light transmitting resin, polypropylene, polyethylene or polyvinyl alcohol can be used.

It is preferred that an ultraviolet light reflecting portion 79 be provided, in order to reflect the portion of the ultraviolet light irradiated from the ultraviolet light source 78 that is not directed straight to the inner tube 46, thereby increasing the ultraviolet light directed toward the inner tube 46. When an ultraviolet light emitting diode is used as the ultraviolet light source 78, as shown in FIG. 5(a), the irradiation range of the ultraviolet light source 78 is limited, and it is difficult to secure sufficient ultraviolet light directed straight toward the inner tube 46. Therefore, in such a case, it is particularly preferred that the ultraviolet light reflecting portion 79 be provided. The ultraviolet light reflecting portion 79 may be used even if a mercury lamp is used as the ultraviolet light source 78.

If the ultraviolet light reflecting portion 79 is provided only at a portion of the interior of the joint portion 15 which does not face the inner tube 46 in the radial direction, it is possible to reflect the ultraviolet light not directed straight toward the inner tube 46.

In cases where the tip portion 74 formed in the shape of a hemisphere is used, for example, the ultraviolet light reflecting portion 79 is preferably provided along the hemispheric inner surface of the tip portion 74, to increase the amount of the ultraviolet light directed toward the inner tube 46. It is not necessary to provide the ultraviolet light reflecting portion 79 on the entire region of the portion of the interior of the joint portion which does not face the inner tube 46 in the radial direction. For example, if the formation of the ultraviolet light reflecting portion 79 causes problems in forming the water flow hole 75, the ultraviolet light reflecting portion 79 may be provided only on the inner surface of the tip portion 74.

For example, the ultraviolet light reflecting portion 79 can be provided at the interior of the joint portion 15 by insert molding of a metal foil when the joint portion 15 is formed by molding of a resin.

Alternatively, the ultraviolet light reflecting portion 79 may be a metal layer adhered to the inner surface of the joint portion 15 by vacuum deposition or plating. In this case, as shown in FIG. 5(b), the metal layer is preferably adhered to an uneven surface of the joint portion 15 formed by molding of a resin. Since the ultraviolet light reflecting portion 79 thus formed has a reflecting surface formed along the uneven surface of the joint portion 15, it causes the irregular reflection of the ultraviolet light irradiated from the ultraviolet light source 78. This irregular reflection is more effective in increasing the amount of ultraviolet light directed toward the inner tube 46, compared to the reflection provided by the ultraviolet light reflecting portion 79 having a smooth surface, as shown in FIG. 5(a).

Of the inner tube 46, at least the guiding cylindrical portion 50 is preferably sterilized, and more preferably, the fastening belt portion 49 is also sterilized. It is preferred that the portion of the guiding cylindrical portion 50 closer to the stepped portion 48 receive the largest amount of the ultraviolet light irradiated.

When a mercury lamp is used as the ultraviolet light source 78, as shown in FIG. 5(c), the ultraviolet light source 78 is disposed so as to face the inner tube 46 in the radial direction. This allows for increasing the amount of ultraviolet light irradiated from the ultraviolet light source 78 and directed straight toward the gap between the guiding cylindrical portion 50 and the straight portion 73, and toward the fastening belt portion 49, compared to that in the embodiment in which the ultraviolet light emitting diode is used as the ultraviolet light source 78. In addition, it is also possible to eliminate the need to provide the ultraviolet light reflecting portion. Even if the ultraviolet light reflecting portion 79 is provided, as shown in FIG. 5(a) and FIG. 5(b), a portion of the reflected light is unable to reach the gap between the guiding cylindrical portion 50 and the straight portion 73, interfered with by the stepped portion 48. Therefore, if high sterilization efficiency is required especially in the vicinity of the guiding cylindrical portion 50 and the stepped portion 48, it is preferred that the ultraviolet light source 78 be a mercury lamp disposed so as to face the inner tube 46 in the radial direction, over the range extending from the fastening belt portion 49 to the guiding cylindrical portion 50, as shown in FIG. 5(c).

As shown in FIG. 5(a), the joint portion 15 is fixed to a cup member 80 surrounding the joint portion 15. The cup member 80 is a tubular member having a bottom portion and opens toward the raw water container 4, and the joint portion 15 extends through the bottom portion of the cup member 80 in a horizontal direction. A tapered surface 81 is formed at the opening edge of the cup member 80. The diameter of the tapered surface 81 increases toward the raw water container 4. The tapered surface 81 guides the neck portion 43 toward the position of the joint portion 15, even if, as shown by the chain line in FIG. 4, the neck portion 43 of the raw water container 4 is not accurately aligned with the joint portion 15 when stowing the raw water container 4 into the housing 1.

The ultraviolet light source 78 may be configured to be turned on at all times while the power of the water dispenser is turned on, or alternatively, the ultraviolet light source 78 can be configured to be controlled by a timer so as to be, for example, turned on and off at regular intervals. The ultraviolet light source 78 is preferably controlled so as to be turned on and off at regular intervals, especially in order to prevent the ultraviolet light irradiated therefrom from getting in the eyes of an operator, when the raw water container is replaced.

In addition, it is preferred that: the cold water tank 2 be housed in the upper portion of the housing 1; the loading space 12 into and out of which the raw water container 4 can be moved, and the door 13 for opening and closing the loading space 12, be provided at the lower portion of the peripheral wall 10 of the housing 1; the peripheral wall 10, including the door 13, be made of a material which does not transmit ultraviolet light irradiated from the ultraviolet light source 78; and the joint portion 15 be disposed in the rear portion of the loading space 12 in the housing 1 so as to be detachably connected to the water outlet port 14. The joint portion 15, disposed in the rear portion of the loading space 12, is difficult for an operator to visually confirm, not only while the raw water container 4 is stowed inside the lower portion of the housing 1, but also when the raw water container 4 is replaced. Therefore, even when the power of the ultraviolet light source 78 is on, the operator can carry out the replacement of the raw water container 4 without getting ultraviolet light into his/her eyes.

The joint portion 15, which is disposed in the loading space 12 so as to be detachably connected to the water outlet port 14, is not limited to the fixed type as in this embodiment, but may, for example, be configured such that the sliding movement of the container receiver 5 into the loading space 12 is converted into the vertical movement of the joint portion 15, so that the joint portion 15 can be inserted into the inner tube 46 of the raw water container 4 when the raw water container 4 is stowed in the rear portion of the loading space 12 in the housing 1. The peripheral wall 10, including the door 13, is made of a metal plate or a colored resin, as appropriate, and provided so as not to transmit the ultraviolet light irradiated form the ultraviolet light source 78.

It is now described how the above described water dispenser is used. In the normal operation mode shown in FIG. 1, when a user of the water dispenser operates the cold water cock 28 to discharge low temperature drinking water in the cold water tank 2 into a cup or the like, the water level in the cold water tank 2 falls. When the user operates the hot water cock 38 to discharge high temperature drinking water in the hot water tank 3 into a cup or the like, too, the water level inside the cold water tank 2 falls, because the same amount of drinking water as the discharged high temperature drinking water is introduced from the cold water tank 2 into the hot water tank 3 through the tank connecting passage 8. When the water level sensor 25 detects that the water level in the cold water tank 2 has fallen below a predetermined lower limit, the pump 7 is actuated and pumps up drinking water from the raw water container 4 to the cold water tank 2.

As drinking water in the cold water tank 2 or the hot water tank 3 is used, the drinking water in the raw water container 4 gradually decreases and the raw water container 4 eventually becomes empty. When the raw water container 4 becomes empty, and the flow rate sensor 16 detects that drinking water is not flowing in the raw water supply passage 6 while the pump 7 is in operation, a container-replacement lamp placed on the front surface of the housing 1, which is not shown, is turned on to notify the user that the raw water container 4 needs to be replaced.

When the raw water container 4 becomes empty, the user replaces the raw water container 4 as follows. First, as shown in FIG. 4, the door 13 is pulled forward to move the container receiver 5 out of the housing 1. At this time, the raw water container 4 is disconnected from the joint portion 15 fixed inside the housing 1, since the raw water container 4 moves together with the container receiver 5. Then the empty raw water container 4 is removed from the container receiver 5. A fully filled raw water container 4 is then placed on the container receiver 5 with the neck portion 43 of the raw water container 4 facing sideways such that the neck portion 43 of the raw water container 4 is fitted to the notch 70 of the container receiver 5. Finally, the door 13 is pushed back to stow the container receiver 5 into the housing 1. At this time, since the raw water container 4 moves together with the container receiver 5, the raw water container 4 is connected to the joint portion 15 fixed within the housing 1.

Since, as shown in FIG. 7, the water dispenser is configured such that when the raw water container 4 is connected to the joint portion 15, the water flow hole 75 never covers the entire axial width of the fastening belt portion 49, and the gap between the guiding cylindrical portion 50 and the straight portion 73 does not communicate with the interior of the raw water container 4, the leaking of water into the gap can be avoided, thereby preventing the proliferation of bacteria therein.

Figure 8:
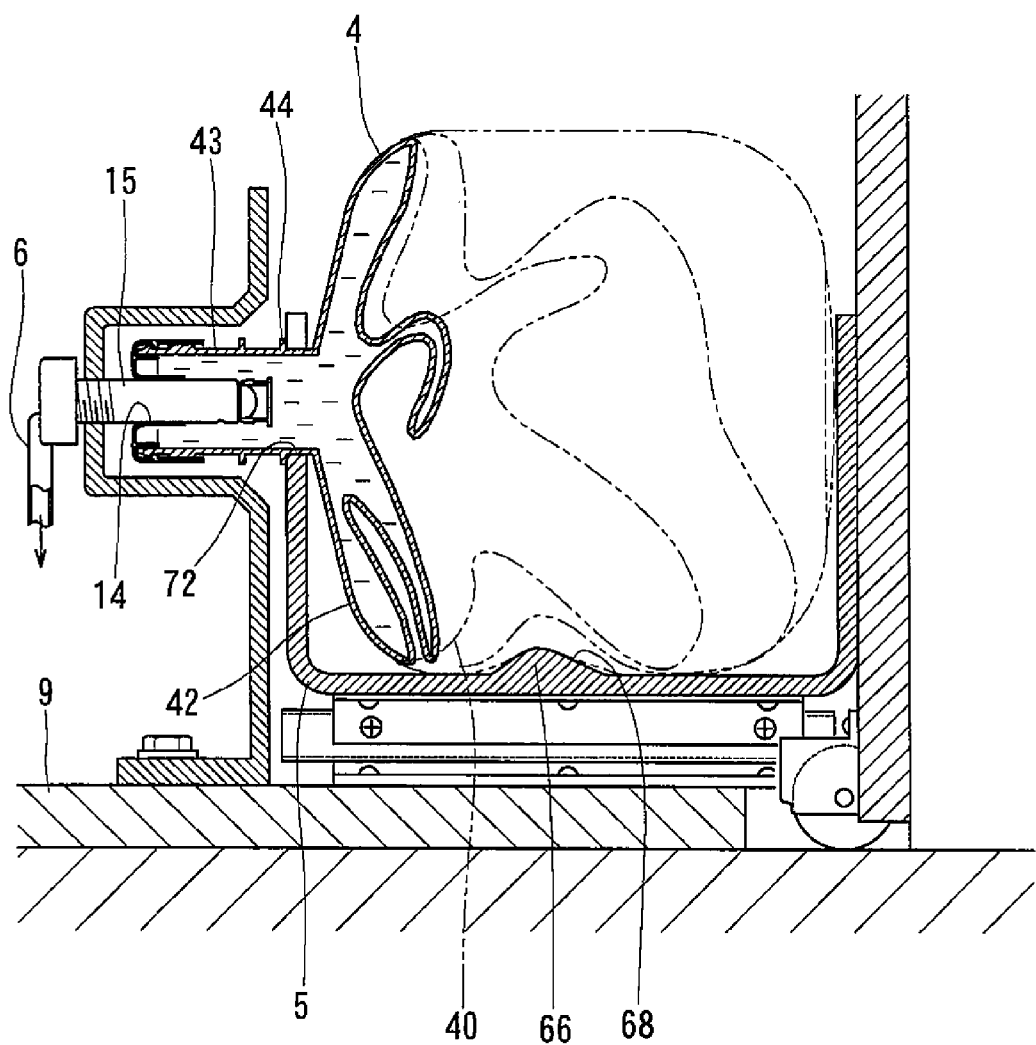
FIG. 8 is a sectional view of the water dispenser shown in FIG. 2, illustrating the process in which the raw water container gradually collapses.
Figure 9:
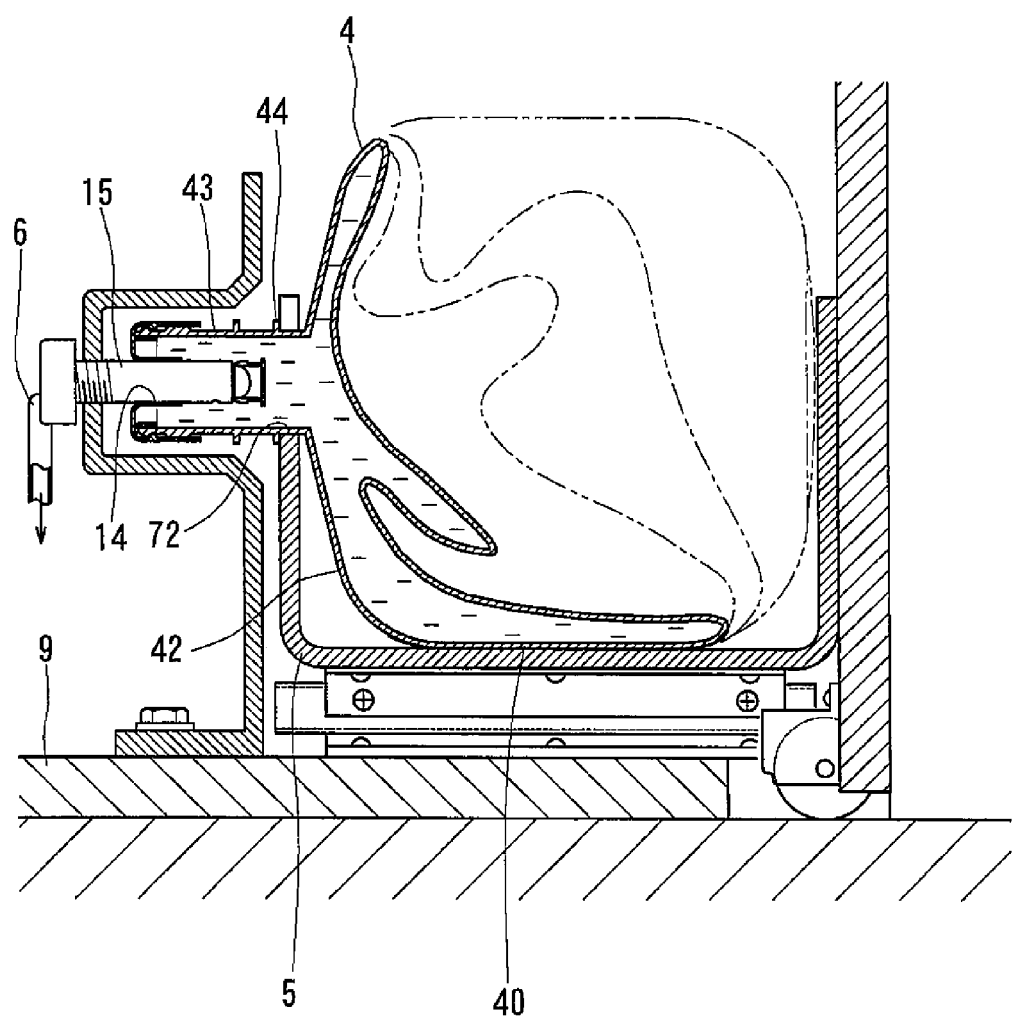
FIG. 9 is a sectional view of the water dispenser shown in FIG. 2, illustrating the process in which the raw water container gradually collapses, when the container receiver is not provided with a protrusion.

As shown in FIG. 8, the raw water container 4 collapses due to atmospheric pressure, as the drinking water inside the raw water container 4 is pumped out by the pump 7. The protrusion 66 provided on the bottom plate of the container receiver 5 allows the raw water container 4 to be collapsed in an optimum manner, such that the drinking water in the raw water container 4 can be pumped out as much as possible, leaving only a minimum amount of water in the raw water container. In particular, when a fully filled raw water container 4 is placed on the container receiver 5, the portion of the trunk portion 40 of the raw water container 4 which comes into contact with the bottom plate of the container receiver 5 is folded along the protrusion 66, and not stretched. Thus, when the drinking water in the raw water container 4 is pumped out by the pump 7, the portion of the trunk portion 40 of the raw water container 4 in contact with the bottom plate is deformed so as to be folded inward, due to the pressure reduction inside the raw water container 4 (see the chain line shown in FIG. 8). As a result, drinking water is less likely to remain in the portion of the raw water container 4 in contact with the bottom plate when the raw water container 4 is collapsed, thereby allowing for the reduction in the amount of water left in the raw water container 4, when the raw water container 4 is replaced.

Further, the raw water container 4 is disconnected from the joint portion 15, which is the end portion of the pumping pipe 6a of the raw water supply passage 6, when the container receiver 5 is pulled out of the housing 1; and the raw water container 4 is connected to the joint portion 15 when the container receiver 5 is stowed inside the housing 1. In other words, it is not necessary to configure the pumping pipe 6a so as to follow the movement of the container receiver 5. As a result, in the above mentioned water dispenser, the length of the pumping pipe 6a can be made short, thereby preventing the proliferation of bacteria in the pumping pipe 6a.

Since, in the above mentioned water dispenser, the pumping pipe 6a is not required to follow the movement of the container receiver 5, it is not necessary to use a spiral tube or a flexible tube for the pumping pipe 6a, and a rigid one can be used as the pumping pipe 6a. Thus, a metal pipe (such as a stainless steel pipe and a copper pipe) excellent in oxygen barrier properties and heat resistance can be used as the pumping pipe 6a.

In addition, in the above mentioned water dispenser, it is possible to sterilize the pumping pipe 6a and to secure the sanitation of the water dispenser for a long period of time, by performing sterilization operation regularly. The sterilization operation of the water dispenser will be described below. First, as shown in FIG. 10, the first switching valve 17 is switched to allow communication between the first bypass pipe 18 and the pump 7, and the second switching valve 19 is switched to allow communication between the pumping pipe 6a and the second bypass pipe 20. Then, the pump 7 is actuated. This allows high temperature drinking water in the hot water tank 3 to pass through the first bypass pipe 18, the first switching valve 17, the pumping pipe 6a, the second switching valve 19, and the second bypass pipe 20, sequentially, and to return to the hot water tank 3. In other words, high temperature drinking water in the hot water tank 3 circulates through the pumping pipe 6a. By energizing the heating device 39 of the hot water tank 3 at this time, it is possible to maintain the temperature of the circulating drinking water at a high temperature suitable for sterilization. Thus, the drinking water inside the pumping pipe 6a, the inner surface of the pumping pipe 6a, and the interior of the pump 7 can be sterilized by heat. After the completion of the sterilization operation, the pump 7 is stopped, and the first switching valve 17 is switched to allow communication between the joint portion 15 and the pump 7, and the second switching valve 19 is switched to allow communication between the pumping pipe 6a and the cold water tank 2, as shown in FIG. 1, to return to the normal operation mode. After the completion of the sterilization operation and before returning to the normal operation mode, the first switching valve 17 can be switched to the sterilization operation mode to allow communication between the first bypass pipe 18 and the pump 7, while the second switching valve 19 can be switched to the normal operation mode to allow communication between the pumping pipe 6a and the cold water tank 2; and the pump 7 can be actuated for a predetermined period of time in this state. With this arrangement, high temperature drinking water flows from the pumping pipe 6a into the cold water tank 2, thereby allowing for the sterilization of the portion of the pumping pipe 6a between the second switching valve 19 and the cold water tank 2. At this time, a predetermined amount of high temperature drinking water flows into the cold water tank 2. However, the baffle plate 24 prevents the drinking water in the cold water tank 2 from being stirred, and air surrounded by the suspended wall 26 of the baffle plate 24 prevents the heat transfer from the upper side to the lower side of the baffle plate 24, and thus the drinking water accumulated in the lower portion of the cold water tank 2 can be maintained at a low temperature. By regularly performing the sterilization operation as described above, it is possible to sterilize the pumping pipe 6a, through which the normal temperature drinking water flows during the normal operation mode, and to secure the sanitation of the water dispenser for a long period of time.

If a type of raw water container formed rigid overall is used as the raw water container 4, and if this raw water container 4 is placed with the water outlet port 14 of the raw water container 4 directed horizontally, it is difficult to pump out the drinking water in the raw water container 4 by the pump 7. In contrast, if a raw water container formed flexible so as to be collapsible as the amount of water remaining in the raw water container decreases is used as the raw water container 4, as in the case of the above mentioned water dispenser, the drinking water in the raw water container 4 can be pumped out by the pump 7 even when the raw water container 4 is placed with the water outlet port 14 of the raw water container 4 directed horizontally.

In the above mentioned water dispenser, since the movement of the water outlet port 14 of the raw water container 4 is restricted by the restricting portion 72 of the container receiver 5, when the water outlet port 14 of the raw water container 4 is connected to the joint portion 15, it is possible to prevent the situation where the position of the water outlet port 14 becomes unstable due to the deformation of the raw water container 4 which is formed flexible.

Further, in the above mentioned water dispenser, since the pumping pipe 6a is provided such that it passes through a position lower than the position of the joint portion 15, and the pump 7 is disposed in the pumping pipe 6a at its portion lower than the joint portion 15, when the water outlet port 14 of the raw water container 4 is disconnected from the joint portion 15, it is possible to prevent the drinking water remaining in the pumping pipe 6a from flowing out of the joint portion 15 due to its own weight.

Since the water flow hole 75 of the joint portion 15 of the above mentioned water dispenser is positioned at a relatively low position in the joint portion 15 (in the bottom half region), it is possible to pump out the drinking water in the raw water container as much as possible, even when the amount of drinking water left in the raw water container 4 is decreased. Besides, since the water flow hole 75 does not exist in the upper half portion of the joint portion 15, it is possible to prevent air from flowing into the interior of the joint portion 15, and to prevent drinking water inside the joint portion 15 from flowing out, when the raw water container 4 is disconnected from the joint portion 15.

Further, in the above mentioned water dispenser, since the through hole 76 is formed at the tip of the joint portion 15, when the plug 47 is fitted to the tip portion 74 of the joint portion 15, as shown in FIG. 6 and FIG. 7, air in the space defined between the plug 47 and the tip portion 74 escapes into the joint portion 15 via the through hole 76. This allows the plug 47 to be smoothly fitted to the tip portion 74 of the joint portion 15.

If the diameter of the through hole 76 is set to 1.0 mm or less, more preferably, 0.8 mm or less, when the raw water container 4 is disconnected from the joint portion 15, it is possible to prevent air from flowing into the interior of the joint portion 15 via the through hole 76 by the surface tension of the water, and to prevent drinking water inside the joint portion 15 from flowing out through the water flow hole 75.

In the above mentioned water dispenser, since the tapered surface 81 is provided around the joint portion 15 and configured to guide the neck portion 43 of the raw water container 4 toward the joint portion 15, the raw water container 4 can be connected to the joint portion 15 in a reliable manner.

Although the flange 44 is formed at the neck portion 43 of the raw water container 4 in the above mentioned water dispenser, the flange 44 can be formed on the cap 45 which is attached to the neck portion 43. Alternatively, the flange may not be formed on the neck portion 43 of the raw water container 4, and a clamping means to hold the neck portion 43 can be provided on the container receiver 5 instead, and the clamping means can be used to restrict the movement of the water outlet port 14 of the raw water container 4.

If the container receiver 5 is configured to be moved into and out of the housing 1 in the forward and rearward direction as in the above mentioned water dispenser, the installation space of the water dispenser can be reduced. However, it is also possible to configure the container receiver 5 so as to be movable into and out of the housing 1 in the right and left direction.

In the above mentioned embodiment, an example of the water dispenser is described, in which, as the raw water container 4, a container is used which includes the hollow cylindrical trunk portion 40, the bottom portion 41 provided at one end of the trunk portion 40, and the neck portion 43 provided at the other end of the trunk portion 40 through the shoulder portion 42, wherein the cap 45 is attached to the neck portion 43. However, the raw water container 4 may be a bag made of a resin film and provided with a connecting member including a water outlet port, attached thereto by heat welding or the like, or such a bag placed in a corrugated carton (so called "bag-in-box"). The scope of the present invention is not limited to the above mentioned embodiments, and the present invention includes all of the alterations and variations falling within the technical scope of the claims. For example, the raw water container can be placed such that the water outlet port thereof is directed downward, or a mechanism to transfer water by gravity can be used, as in the water dispensers disclosed in Patent Documents 1 to 4.

DESCRIPTION OF SYMBOLS

2 cold water tank
4 raw water container
6 raw water supply passage
14 water outlet port
15 joint portion
43 neck portion
45 cap
46 inner tube
47 plug
48 stepped portion
49 fastening belt portion
50 guiding cylindrical portion
51 bottomed cylindrical portion
52 fitting surface
53 engaging portion
73 straight portion
74 tip portion
75 water flow hole
78 ultraviolet light source

The invention claimed is:

1. A water dispenser comprising: a replaceable raw water container; a cold water tank; and a raw water supply passage which allows communication between the raw water container and the cold water tank;

wherein a cap is attached to the raw water container, the cap comprising: an inner tube protruding into an interior of the raw water container and defining a water outlet port of the raw water container; and a plug closing the water outlet port;

wherein the raw water supply passage includes a joint portion configured to be detachably connected to the water outlet port;

wherein an inner peripheral surface of the inner tube is provided with a stepped portion having a smaller diameter at a portion thereof closer to the interior of the raw water container, and a fastening belt portion formed contiguous to the stepped portion on a smaller diameter side thereof;

wherein the plug comprises: a bottomed cylindrical portion having a bottom and configured to be fitted to the inner tube with an opening thereof facing an exterior of the raw water container; a fitting surface formed on an outer peripheral surface of the bottomed cylindrical portion so as to be fitted to the fastening belt portion with an interference fit; and an engaging portion formed on the outer peripheral surface of the bottomed cylindrical portion so as to engage with the stepped portion;

wherein the joint portion comprises a cylindrical member including a straight portion configured to be fitted to the fastening belt portion with an interference fit; and a tip portion configured to be fitted inside the bottomed cylindrical portion such that the plug is stably engaged with the tip portion;

wherein the straight portion is provided with a water flow hole configured to open to the interior of the raw water container at a position away from the inner tube; and wherein the water flow hole is formed in a size so as not to cover the entire axial width of the fastening belt portion, while the straight portion is being inserted into the fastening belt portion.

2. The water dispenser according to claim 1, wherein an ultraviolet light source is provided inside the joint portion;

wherein the straight portion is made of an ultraviolet light transmitting resin capable of transmitting ultraviolet light; and wherein the ultraviolet light source is configured to emit ultraviolet light which transmits through the straight portion and sterilize the inner peripheral surface of the inner tube.

* * * * *